(12) United States Patent
Alexander et al.

(10) Patent No.: US 6,309,392 B1
(45) Date of Patent: Oct. 30, 2001

(54) SYSTEM FOR INTRAMEDULLARY FIXATION OF LONG BONE FRACTURES

(76) Inventors: Daniel Alexander, 22728 Heather Brae Way, Novi, MI (US) 48375; Terrence R. Burns, 47 Smallwood Dr., Snyder, NY (US) 14226; John Rooney, 25 N. Long St., Williamsville, NY (US) 14221

(*) Notice: Subject to any disclaimer, the term of this patent is extended or adjusted under 35 U.S.C. 154(b) by 0 days.

(21) Appl. No.: 09/474,701

(22) Filed: Dec. 29, 1999

Related U.S. Application Data

(60) Provisional application No. 60/114,263, filed on Dec. 30, 1998.

(51) Int. Cl.[7] .................................................. A61B 17/72
(52) U.S. Cl. ................................................ 606/64; 606/98
(58) Field of Search .................................. 606/62, 64, 98, 606/63, 67, 96, 104

(56) References Cited

U.S. PATENT DOCUMENTS

| | | |
|---|---|---|
| 4,781,181 | 11/1988 | Tanguy . |
| 5,603,715 * | 2/1997 | Kessler ..................................... 606/62 |
| 5,810,820 * | 9/1998 | Santori et al. ........................... 606/64 |
| 5,814,047 * | 9/1998 | Emilio et al. ............................ 606/73 |
| 5,971,986 * | 10/1999 | Santori et al. ........................... 606/72 |
| 5,993,456 * | 11/1999 | Speitling et al. ....................... 606/64 |

FOREIGN PATENT DOCUMENTS 40 33 280 A 1    10/1991 (DE) .

* cited by examiner

*Primary Examiner*—Cary E. O'Connor
(74) *Attorney, Agent, or Firm*—Howard M. Ellis

(57) ABSTRACT

An intramedullary device facilitates fixation after installing in a bone cavity by drilling a pilot opening from the interior of the device through the bone cortical to the exterior. The intramedullary device is equipped with an internal baffle system which is a stationary and can remain a permanent fixed element of the rod for unimpeded steering of a cutting tool from the interior of the device through the bone cortical to the bone exterior. The interior baffle may consist of a laterally inclined chute allowing a bone boring tool on an elongated power transmission cable to be guidedly advanced downwardly to the interior of the device to a pin opening for cutting the bone cortical from the inside and forming the all important initial pilot opening in the bone. The pilot opening can then be utilized to form a continuous channel by introducing a drill bit from the outside of the bone through the two predrilled openings in the device and then cutting through the opposite bone cortical. A pin is inserted to complete the fixation of the intramedullary device to the bone. Additional fixation pins may thereafter be installed as required. The improved system facilitates the otherwise difficult process of fixation of an intramedullary device, thereby shortening operating and anesthesia times, and decreasing the need for intraoperative x-rays.

20 Claims, 5 Drawing Sheets

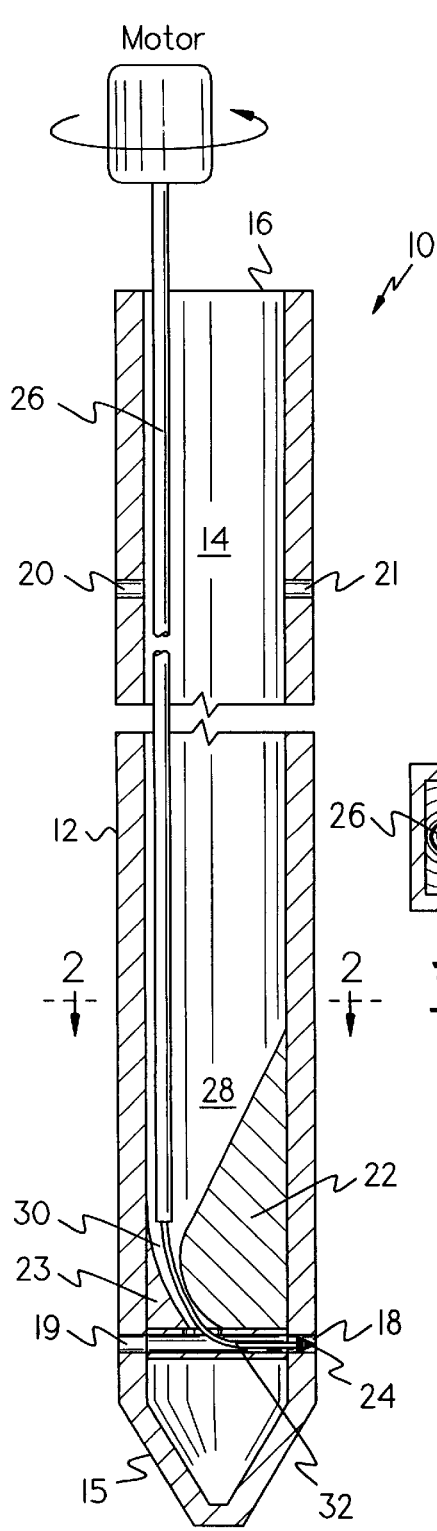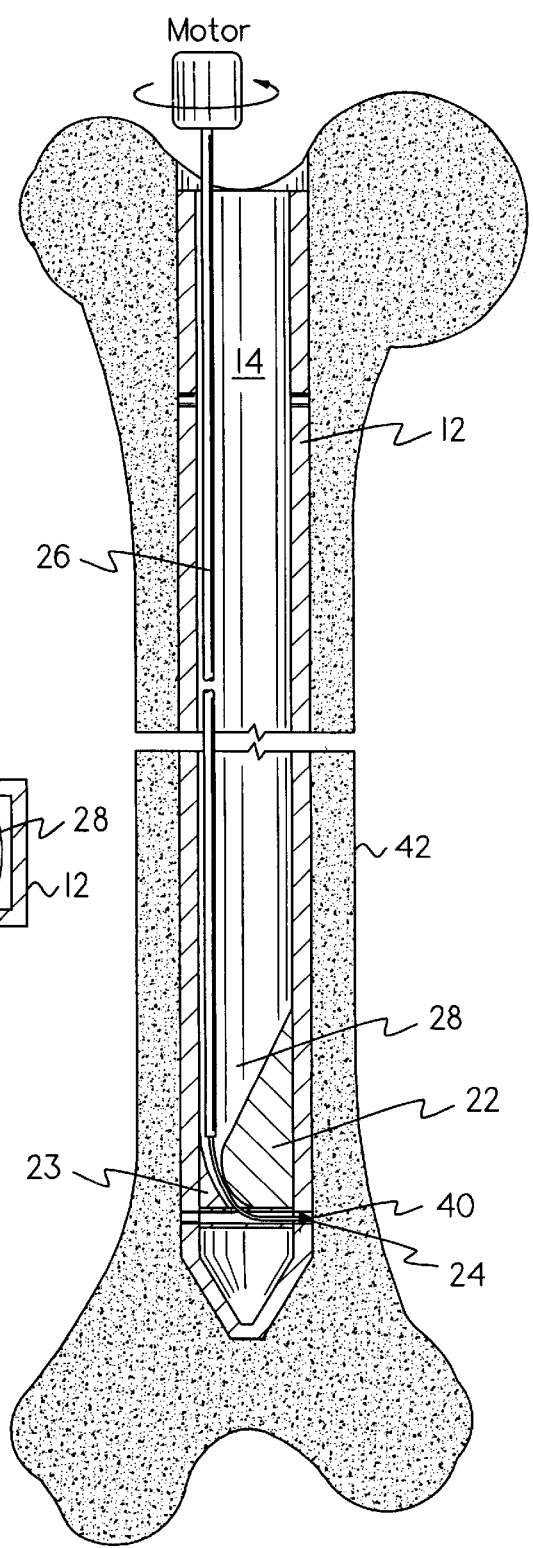

SYSTEM FOR INTRAMEDULLARY FIXATION OF LONG BONE FRACTURES

CROSS REFERENCE TO RELATED APPLICATION

This application claims the benefit of U.S. Provisional Application 60/114,263, filed Dec. 30, 1998.

FIELD OF THE INVENTION

The present invention relates to an orthopedic device, and more specifically, to an improved intramedullary rod and simplified system for securing the device in the medullary cavity of an injured/traumatized bone.

BACKGROUND OF THE INVENTION

Long skeletal structures and especially large weight supporting bones, e.g., tibia, femur, humerus and radius, when fractured often require the introduction of a rod-like device into the medullary canal as a supporting structure and means for repairing the fracture. Current orthopedic practice calls for the introduction of the metal rod or intramedullary device down through the canal of the broken bone to aid in holding the fractured portions together. The rod must then be secured to the bone using either a pin, a nail, bolt or screw, to prevent slippage in the medullary canal when under stress. This is usually carried out first by forming a continuous channel consisting of a predrilled transverse hole in the distal end of the rod and through adjacent corticals of the injured bone. Through such a continuous channel a pin is introduced to affix the rod to the bone.

However, most processes for fixation of the rod require the surgeon to drill "blindly" into the bone from the outside wall in an effort to locate the predrilled hole in the rod. The process of drilling holes in bone which are aligned with the predrilled holes in the rod is inexact, and often performed on a trial and error basis. Consequently, the fixation of an intramedullary device can be and often is a tedious and time consuming process. This also translates into protracted operating room times, added risk to the patient due to longer anesthesia times, risk of further tissue damage, external scarring and increased radiation exposure to the patient and providers.

Various alternative methods for fixation of intramedullary rods have been proposed in an effort to overcome the foregoing problems. For example, fluoroscopy has been used by surgeons for visualization of the predrilled holes in the rod for more accurate drilling of bone. However, fluoroscopy provides only two dimensional images of a three dimensional target, and consequently, the predrilled holes in the rod under the bone are often not visible. Fluoroscopy also means added cost both for the equipment in the operating room and for staffing with an x-ray technician. Laser guidance, plus fluoroscopy, while providing some improvement over fluoroscopy alone, still does not provide consistently reliable images. Other methods have relied on external clamps and drill guides, for example. They too have limitations, including interference by anatomic variations, and less than ideal positioning of the rod in the bone canal making them cumbersome to use.

A further process disclosed by U.S. Pat. No. 4,781,181 to Tanguy provides for positioning an intramedullary rod in the canal of a fractured bone, and with the aid of a boring sensor comprising a translatable drill guiding and positioning unit, a drill bit on a flexible shaft is inserted into the rod interior beginning at the proximal end of the intramedullary rod for drilling a hole from the inside of the bone adjacent to the predrilled opening in the distal end of the rod. While this assures alignment of the predrilled holes in the rod with the holes drilled in the bone for insertion of a pin, before the drill bit can be inserted the boring sensor must be inserted into the rod interior and locked into place at the distal end where it is maneuvered for engaging with a recess in the wall of the rod. The drill bit is then introduced into a sheath in the boring sensor, which performs as a tubular guide routing the drill bit toward the predrilled hole at the distal end of the rod where it is turned laterally toward the bone and drilled from the inside through the cortical end and outwardly. This approach requires additional hardware components, manipulative steps and greater installation time and cost.

Accordingly, there is a need for an improved, more economic intramedullary rod and more efficient and simplified system for fixation of the rod to bone.

SUMMARY OF THE INVENTION

The present invention provides for an improved, more economic intramedullary device which permits drilling bone from the inside of the device with fewer steps and significantly less time and difficulty for the orthopedic surgeon to complete the otherwise tedious task of fixation of the device to bone. The improved intramedullary rod and system for fixation will decrease operating room and anesthesia times, decrease the need for intraoperative x-rays, and reduce the risk of tissue damage and external scarring.

It is therefore one principal object of the invention to provide for an improved intramedullary device which comprises an elongated rod having a wall defining a central cavity. The rod has first and second ends with one or more pairs of oppositely disposed pin openings in the wall. Each pair of the pin openings is aligned in a plane which is transverse to the longitudinal axis of the rod. A baffle means is positioned in the central cavity proximate to the second end for receiving and laterally channeling bone cutting means, such as a drill bit on a elongated flexible drive cable, laser cutting device or practically any other suitable means for precision boring of bone tissue to provide openings in bone tissue adjacent to the pin openings. The baffle means which remains in the central cavity of the rod and is not removed in the fixation process comprises a substantially conically shaped entrance for reliably guided channeling of a flexible power transmission cable and bone cutting means, such as a drill bit to one opening of the pair of pin openings in the wall of the device for boring a pilot opening in the adjacent cortical of the bone from the bone interior. This achieves the necessary alignment for boring a second opening and for completing the needed continuous channel for pinning the intramedullary device to the bone.

More specifically, the baffle means comprises a substantially conically shaped entrance and a tapered laterally displaced chute for guided the bone cutting means and power transmission cable to one of the pin openings in the wall of the rod for boring the all important first pilot opening through the adjacent bone cortical from the rod interior. The curvature of the chute readily allows passage of the cutting tool without binding or crimping the power cable in the process. This first pilot opening from the interior of the bone enables more accurate and efficient boring of a second hole in the opposite cortical from the first pilot opening to complete the needed continuous channel in the fixation of the intramedullary rod.

The improved intramedullary device and system for fixation according to the invention allows for more efficient internal drilling of bone with only the intramedullary rod being required, while eliminating the need for introducing an independent tool, fixture or jig for guiding the introduction of a drilling tool. Generally, the pin openings in the rod may be positioned in a plane which is transverse to the longitudinal axis of the device. This would include pin openings aligned with one another in a plane which is perpendicular or normal to the axis of the rod, or in a diagonal plane. In the case of the latter, this would comprise openings aligned at an acute angle, for example, 45° or less, and more particularly, from about 10 to about 45° measured from the exit point to the rod sidewall.

It is also a further object of the invention to provide a more efficient method for fixation of an intramedullary device to an injured, e.g., fractured bone, which comprises the steps of:

(i) providing an intramedullary device comprising an elongated rod having a wall defining a central cavity. The rod is characterized by first and second ends with one or more pairs of oppositely disposed predrilled pin openings in the wall. Each pin opening of a pair is aligned with the other and lies in a plane which is generally transverse to the longitudinal axis of the rod. The device includes baffle means positioned and remaining only within the central cavity of the rod proximate to the second end of the rod for reliably receiving and laterally channeling bone cutting means on a flexible power transmission cable to one opening of a pair of the pin openings. The baffle means comprises a substantially conically shaped entrance;

(ii) positioning the intramedullary device into the medullary or interior cavity of the injured bone wherein the second end is the leading end for entry into the bone cavity;

(iii) introducing bone cutting means on a power transmission cable into the central cavity of the positioned intramedullary device beginning at the first end of the rod and thereafter into the conically shaped entrance of the baffle means and into one pin opening of a pair of the pin openings in the wall of the rod;

(iv) boring a first opening in the adjacent cortical of the bone for receiving a fixation pin;

(v) introducing bone cutting means from the bone exterior, through the first opening made in the bone cortical in step (iv) and then through a first and second predrilled openings of the pair of pin openings in the intramedullary device and then against the bone cortical adjacent to the second predrilled opening of the device;

(vi) boring a second opening in the adjacent cortical of the bone for receiving a fixation pin, and (vii) introducing a pin through the aligned openings for fixation of the intramedullary device to the bone.

BRIEF DESCRIPTION OF THE DRAWINGS

For a further understanding of the invention and its characterizing features reference should now be made to the accompanying drawings wherein:

FIG. 1 is an enlarged side elevational view of the intramedullary device of the invention prior to installation showing the geometry of the conically shaped baffle as a guide for the flexible power transmission cable and tool for internal drilling of bone;

FIG. 2 is a top sectional view of the intramedullary device taken along line 2—2 of FIG. 1;

FIG. 3 is a side elevational view of the intramedullary device of FIG. 1 implanted in a large bone, prior to boring the initial pilot opening in the bone:

DESCRIPTION OF THE PREFERRED EMBODIMENTS

Figures 4, 5:
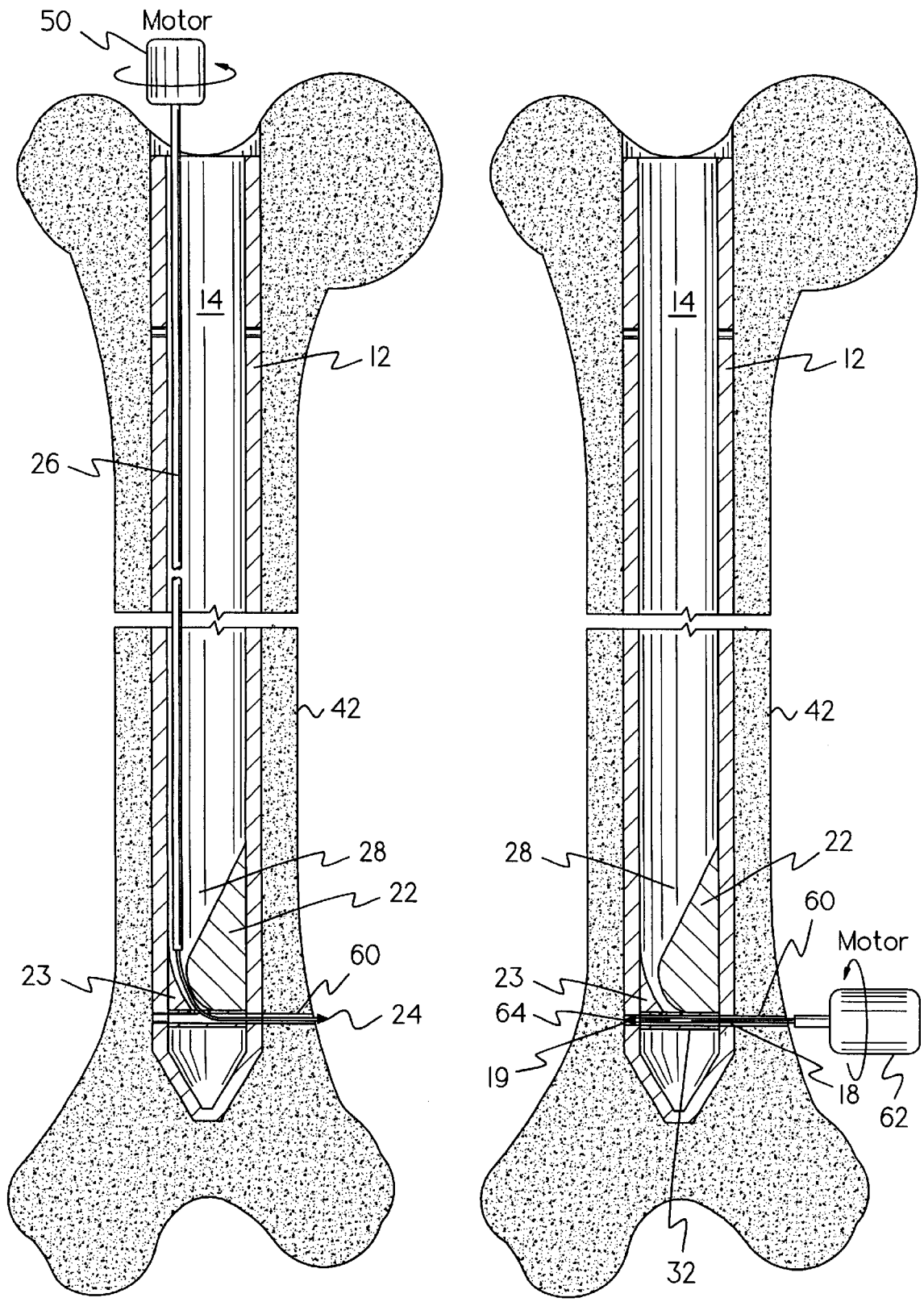
FIG. 4 is a side elevational view of the intramedullary device of FIG. 3 with the internally drilled pilot opening.
FIG. 5 is a side elevational view of the intramedullary device of FIG. 4 prior to drilling the second pin opening in the bone from the outside using the internally drilled pilot opening.

Turning first to FIG. 1, there is shown an intramedullary device 10 represented in sectional view. Generally, device 10 comprises a metallic rod 12, fabricated from such metals as stainless steel, titanium or various alloys used in orthopedic appliances. Structurally, the intramedullary rods can include rectangular cross-sectional configurations although round or generally circular shaped rods are also contemplated. Rectangular shapes are also inclusive of square cross-sectional configurations. Device 10 may also be tapered somewhat at leading end 15 imparting a generally nail-like appearance for facilitating installation as a boring tool, making it more readily insertable by surgeons into the medullary cavity. Rods of the invention also possess other desirable properties of current state of the art intramedullary devices, such as the desired flexibility and safety features, like biocompatibility, and so on. The actual length and diameter of the devices can vary, and will be determined, for example, by the length and girth of the bone being repaired. The rod interior is substantially hollow and includes a central cavity 14, and an open trailing end 16 making the central cavity readily accessible.

At least one pair of pin openings, and more preferably, two or more pairs of pin openings are predrilled into the rod of the intramedullary device. FIG. 1 is illustrated with a pair of distal pin openings 18–19 near the leading end 15 of the device and a pair of proximal pin openings 20–21 at the trailing end 16 of the device. The pin openings are of a dimension sufficient to accommodate pins, usually orthopedic screws, bolts, nails, and other similar type fasteners use in securing orthopedic devices. Each pin opening of a pair is aligned opposite the other and in the same plane, that is transverse to the longitudinal axis of the rod, e.g., either normal to the axis of the device, or alternatively, in a plane which is generally diagonal or inclined obliquely to the plane of the rod. That is, the pin openings generally run in a plane perpendicular to the longitudinal axis of the rod, or aligned in planes which are obtusely or acutely oriented from the plane of the rod.

In the region of the leading end 15 of the device, central cavity 14 comprises baffles 22 and 23 which are components of the device, and not withdrawn in the fixation process. It is to be understood that while the system of baffles is shown with a combination interior baffle structures 22 and 23, the invention also preferably contemplates a one-piece baffle molded to have the desired funnel-like configuration. In each case, the interior baffle system does not exceed the length of the rod so as to extend outwardly from the central cavity. Accordingly, the interior structural elements need not be removed after drilling the required openings in the bone in the fixation process. In fact, the interior baffle may be installed as a permanent fixture or be made integral with the intramedullary rod structure.

The interior baffle system facilitates entry and placement of a boring tool which can be motor driven, such as shown with drill bit 24 on a flexible power transmission cable 26 to distal pin opening 18. The figures illustrate baffle 22 in cooperation with the interior sidewall of the rod and opposing baffle 23 forming a generally conically shaped opening 28 for funneling drill bit 24 and cable 26 towards tapered and rounded chute 30 of the baffle. Because chute 30 is pitched laterally drill bit 24 is directed off-center in the direction of pin opening 18. The rounded configuration of chute 30 avoids binding cable 26 as the drill bit enters pin opening 18. Chute 30 preferable includes a tubular bridging conduit 32 linking the oppositely disposed pin openings 18 and 19. In this first embodiment, chute 30 preferably empties into tubular bridge 32 facilitating threading drill bit 24 to predrilled pin opening 18, so it is flush against the inside cortical 40 of bone 42 (FIG. 3).

Drill motor 50 (FIG. 4), such as a Moto-Flex™ 332 Variable speed drill with flexible cable 26 equipped with ⅛ inch high speed cutting drill 24 available from Dremel Industries, Racine, Wis. will quickly and efficiently cut through bone 42 forming a pilot hole 60, a continuation of the tubular bridge 32 of baffle 22. Thus, the pilot hole is made without x-ray guidance or risk of error in placement of the drill bit because the drill has but one location that it may go.

Figures 6, 7:
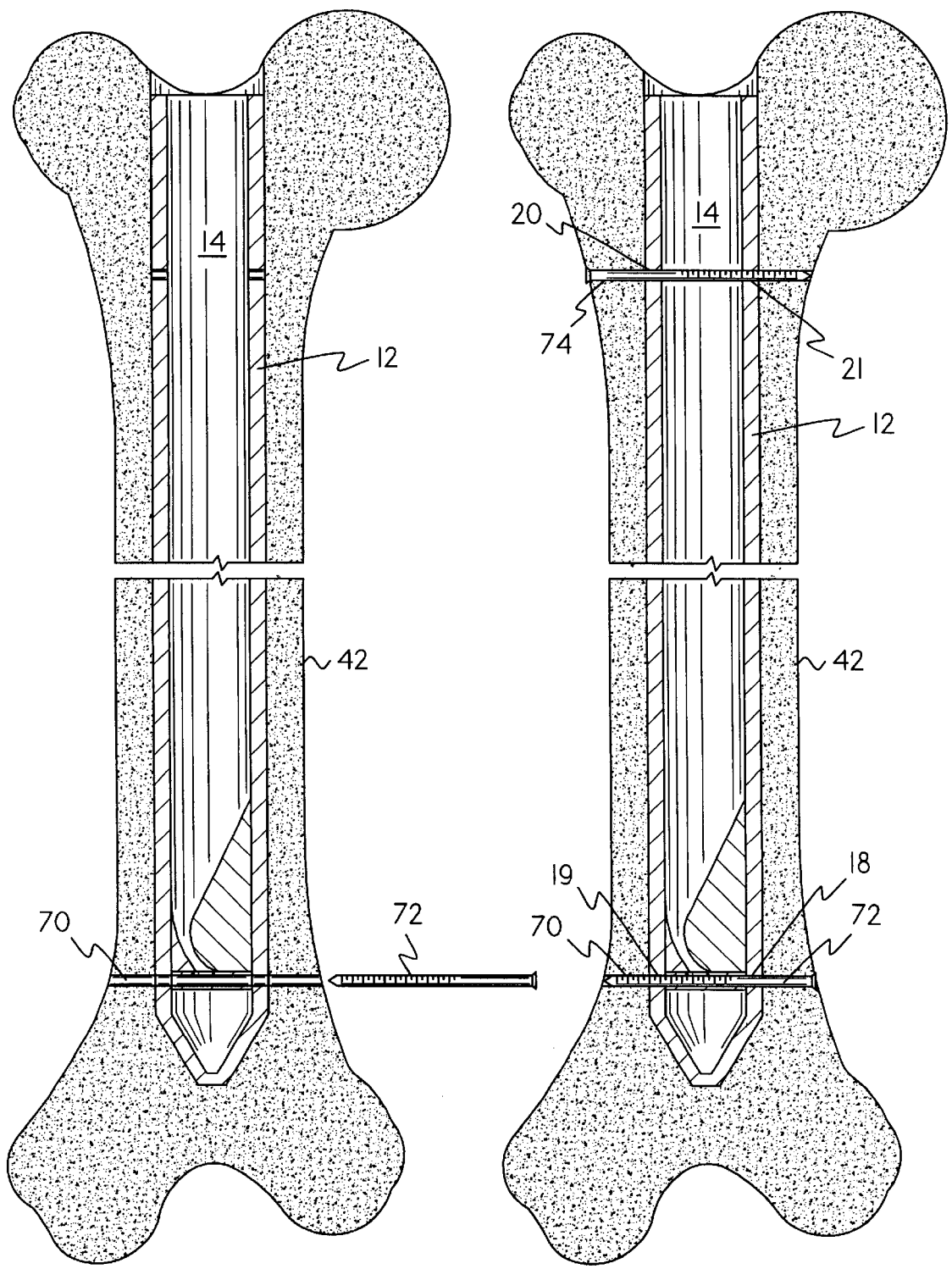
FIG. 6 is a side elevational view of FIG. 5 after the second pin opening has been drilled from the outside with the aid of the pilot opening.
FIG. 7 is a side elevational view of FIG. 6 with pins installed for fixation of the device to the bone.

Drill motor 50, shaft 26 and drill bit 24 are withdrawn from central cavity 14 of the device. In order to create a continuous channel formed by two openings drilled in the bone and predrilled openings 18 and 19 in the intramedullary device, drill 62 (FIG. 5) is introduced first into the pilot opening 60 which allows passage into tubular bridge 32 then into predrilled opening 19 and flush against cortical bone 64. Drill 62 is actuated and a continuous channel 70, best illustrated by FIG. 6, formed by drilling a hole through the remaining bone.

An orthopedic pin 72 of appropriate dimension is introduced into the continuous channel 70 to securely affix the distal end of the intramedullary device to the bone. An additional pin 74 (FIG. 7) can also be installed in the proximal pin openings 20 and 21 near the trailing end of the rod using known methods. For example, predrilled openings 20 and 21 are aligned and in the same perpendicular plane as distal predrilled openings 18 and 19. Furthermore, the distance between each pair of pin openings is provided with each rod. After installation of the distal pin 72 the location of the upper or proximal pin openings 20–21 can be identified by measuring the space from the distal pin to locate the proximal pin openings for drilling of the bone corticals and introduction of proximal pin 74. Other methods include visual inspection of the predrilled openings proximal to the terminal end of the rod which facilitates placement of the proximal locking pin or screw.

In practicing the methods of the invention wherein the device is introduced into the medullary canal of a large fractured bone, such as a femur, it will be understood introduction of the rod into the bone may begin either from the proximal or pelvic end of the bone, or alternatively, the rod may be introduced at the distal or knee end for retrograde insertion.

Figure 8:
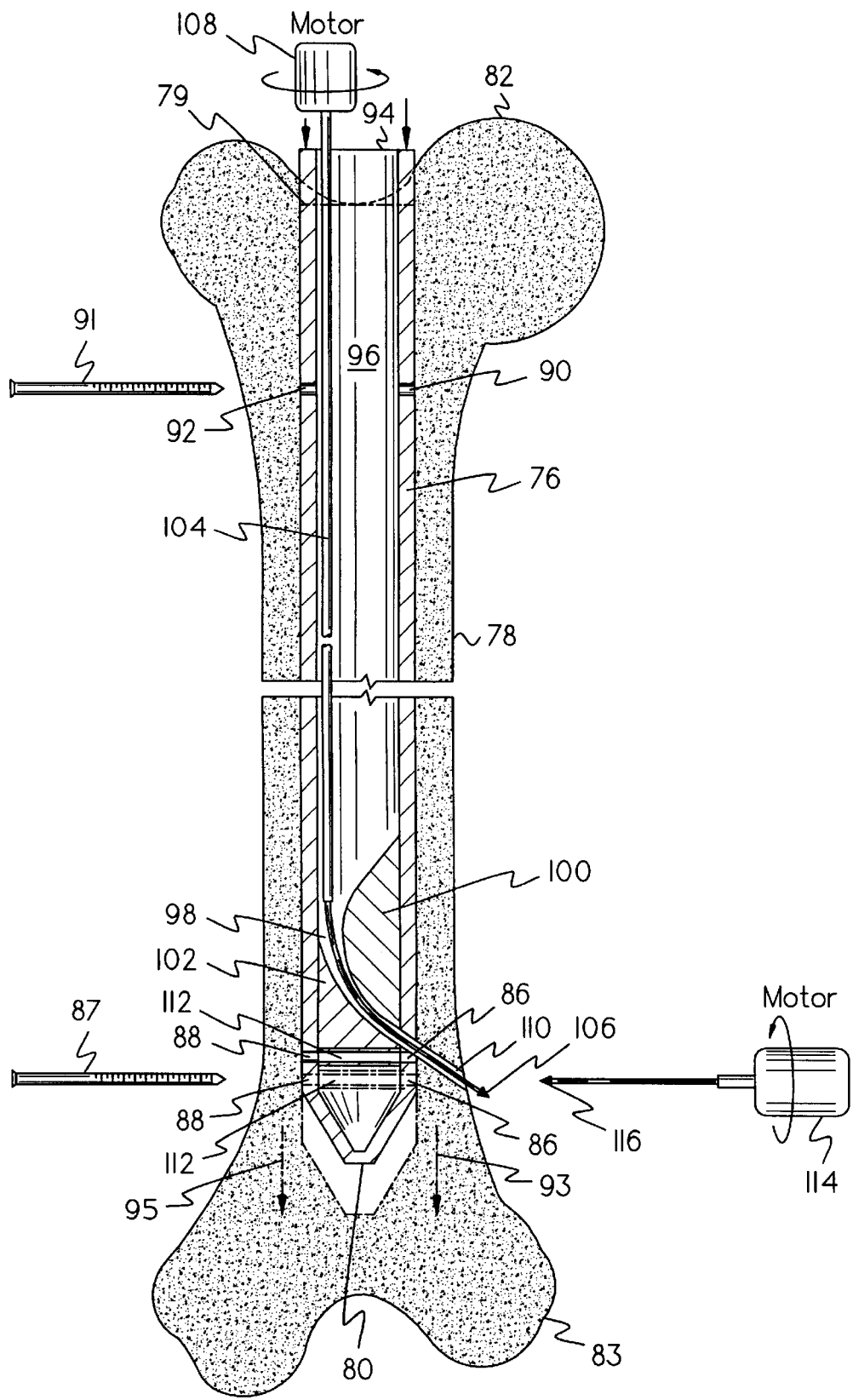
FIG. 8 is a side elevational view of a further embodiment of the invention showing angular boring of bone tissue with two stage introduction of the intramedullary device.
Figure 9:
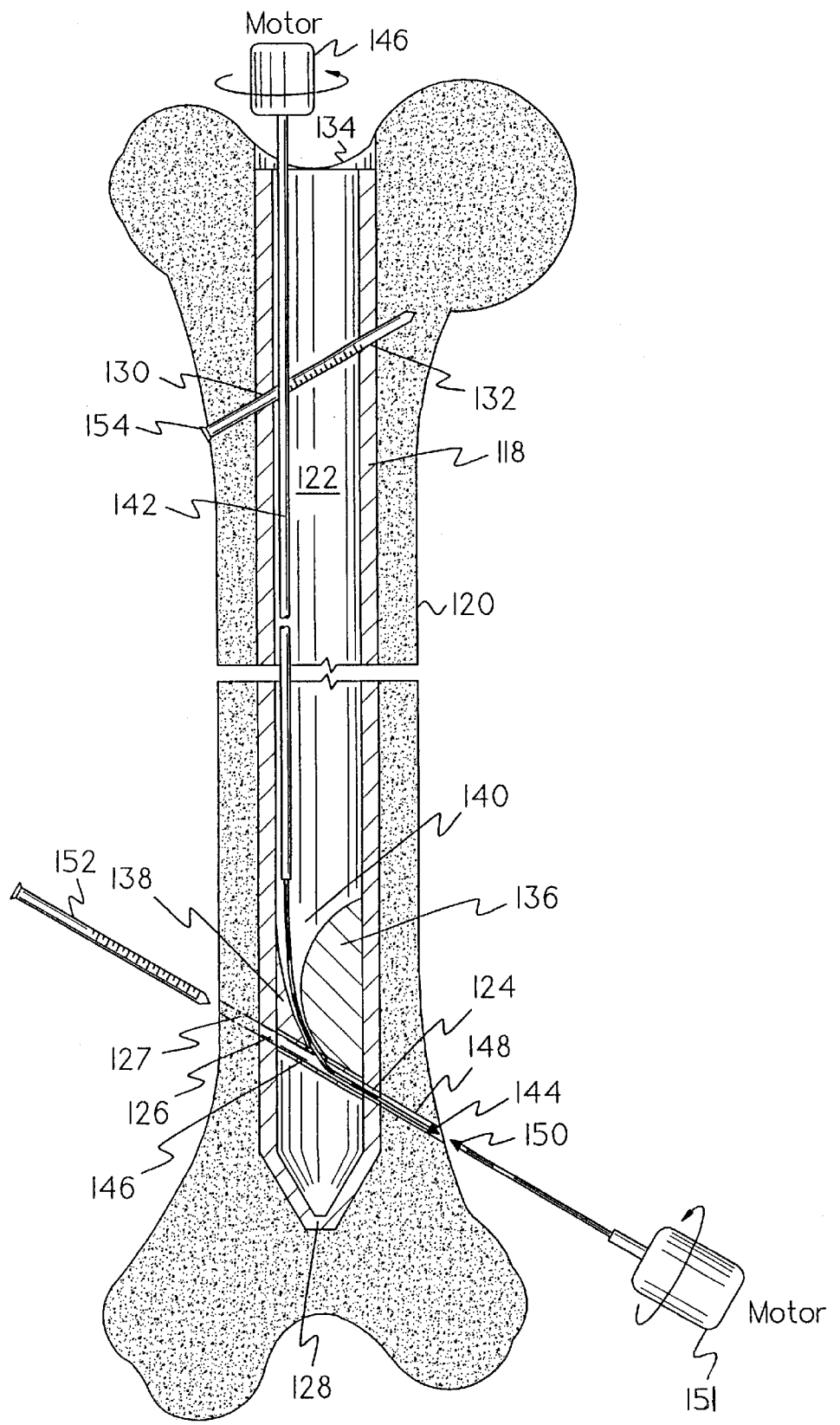
FIG. 9 is a side elevational view of yet a further alternative embodiment of the invention wherein fixation of the intramedullary device is achieved with diagonally positioned pins.

The invention contemplates further embodiments for fixation of intramedullary rods in large bones, such as illustrated by FIGS. 8 and 9. FIG. 8 employs a modified rod 76 inserted into a large bone 78 by a two phase process. Rod 76, also tapered at the leading end 80, is initially inserted into the medullary cavity of bone 78 by customary means with entry beginning either at the proximal end 82, or by retrograde insertion at the distal end 83 of bone 78. Rod 76 is inserted into the medullary cavity of bone 78 until the visible scored stop point guide 79 is even with the proximal end 82 of the bone.

Metallic Rod 76 further comprises at least two pairs of pin openings, a first pair, 86 and 88, near the leading end 80 of rod 76, and second pair of pin openings, 90 and 92, located near the trailing end 94 of the device. Both pairs of pin openings, 86–88 and 90–92, are positioned generally in a normal plane to the longitudinal axis of the rod. Rod interior 96 includes generally conically shaped baffles 100 and 102 affixed to the rod interior and converging into a laterally tapered and rounded chute 98, for threading power transmission cable 104 and boring tool, e.g., drill bit 106, attached thereto, downwardly and diagonally to pin opening 86, so that drill bit 106 is in contact with the inside cortical of bone 78 adjacent to opening 86. Motor 108 is actuated producing an angular pilot hole 110 at approximately a 15° to 45° angle measured from the side wall of the rod.

After drilling pilot hole 110, motorized drill bit 106 and transmission cable 104 are withdrawn from rod interior 96. In a second phase of the installation the rod 76 is tapped further into the medullary cavity by the surgeon, so trailing end 94 of the rod is then even with proximal end 82 of bone 78. This automatically lowers pin openings 86 and 88, and tubular bridge 112, as shown by parallel arrows with broken lines 93 and 95, so they are in alignment with the exterior of pilot hole 110. Motorized drill 114 equipped with boring means, e.g., drill bit 116, is then positioned for normal/transverse drilling from the outside portal of pilot hole 110 for drilling bone, for entry into pin opening 86 and bridge conduit 112, and into pin opening 88. Motorized drill 114 is further actuated boring through the cortical immediately adjacent to pin opening 88. Orthopedic pins 87 and 91 are finally introduced through the drilled openings in the bone corticals for fixation of the rod.

It will be understood that any means for boring holes in bone may be used in addition to drills, including laser cutting devices, ultrasound energy, chemical cutting means, and so on.

The embodiment of FIG. 9 illustrates fixation of an intramedullary rod 118 to a large bone 120 with diagonally positioned pins and an interior system of baffles which eliminates the need for surgeons to introduce special jigs or fixtures for fixation of the rod. The generally nail shaped rod 118 is characterized by a tubular body with a central cavity 122. Pairs of pin openings are employed, including openings 124 and 126 positioned near leading end 128 of rod 118, and a second pair of pin openings 130 and 132 proximate to the trailing end 134 of the rod. Central cavity 122 has affixed therein a system of baffles 136 and 138 spaced sufficiently from one another to define a generally conically shaped chute 140 for directing power transmission cable 142 and boring tool 144, e.g. drill bit, laterally downwardly at interconnecting with bridging conduit member 146 positioned between pin openings 124 and 126, without binding cable 142.

The drill bit 144 engages with the inside cortical of bone 120. Motor 146 is actuated to form pilot opening 148 in bone 120. The cable and drill bit are then withdrawn. Drill bit 150 on an extended power transmission cable and equipped with motor means 151 is introduced into pilot opening 148 from the bone exterior, and an opening 127 is drilled in the opposite cortical adjacent to pin opening 126. Drill bit 150 is withdrawn and an orthopedic nail 152 is introduced into the opening for fixation of the rod to the lower portion of the bone. The drilling process is repeated for upper pin openings 130 and 132. Orthopedic pin 154 is shown inserted into the opening.

While the invention has been described with various embodiments, they are illustrative only. Accordingly, many alternatives, modifications and variations will be apparent to persons skilled in the art in light of the foregoing description, and it is therefore intended to embrace all such alternatives, modifications and variations as to fall within the spirit and broad scope of the appended claims.

We claim:

1. An intramedullary device, which comprises an elongated rod having an outer wall defining an interior cavity, said rod having an open first end, a second end and at least one pair of oppositely disposed pin openings in said outer wall for fixation of said rod to bone tissue, each pair of said pin openings aligned in a plane which is transverse to the longitudinal axis of said elongated rod, and baffle means positioned in said interior cavity for guiding movement of means for boring through bone tissue adjacent to at least one of said pin openings, said baffle means being suitable for remaining in said interior cavity with fixation of said device to said bone tissue.

2. The intramedullary device of claim 1 wherein said open first end of said elongated rod and baffle means are adapted to receive and guide movement of said means for boring through bone tissue in a generally lateral direction toward said outer wall.

3. The intramedullary device of claim 1 wherein said baffle means comprises a narrowing and sloping passage.

4. The intramedullary device of claim 3 wherein said baffle means is characterized by a funneling configuration for guiding said means for boring through bone tissue through rounded conduit means running in a direction generally normal to the longitudinal axis of said outer wall.

5. The intramedullary device of claim 1 comprising a one-piece baffle.

6. The intramedullary device of claim 1 wherein said baffle means comprises a plurality of guides for steering the course of movement of said means for boring bone tissue.

7. The intramedullary device of claim 1 wherein the plane of a pair of said pin openings is inclined obliquely to the longitudinal axis of said elongated rod.

8. The intramedullary device of claim 1 wherein the plane of a pair of said pin openings is positioned substantially normal to the longitudinal axis of said elongated rod.

9. The intramedullary device of claim 1 wherein the rod comprises a substantially nail-like configuration.

10. The intramedullary device of claim 1 including means for measuring depth of insertion of said rod in the medullary cavity of a bone.

11. A method for fixation of an intramedullary device to an injured bone, which comprises the steps of:

(i) providing an intramedullary device comprising an elongated rod having an outer wall defining an central cavity, said rod having an open first end, a second end and at least one pair of oppositely disposed pin openings in said outer wall for fixation of said rod to bone tissue, each pair of said pin openings aligned in a plane which is transverse to the longitudinal axis of said elongated rod, and baffle means positioned in said interior cavity for guiding means for boring through bone tissue adjacent to at least one of said pin openings;

(ii) positioning said intramedullary device into a medullary cavity of said injured bone;

(iii) introducing a bone boring device on a flexible drive shaft into the central cavity of said intramedullary device beginning at the first end of said rod and thereafter into the entrance of said baffle means and for steering said bone boring device to one pin opening of a pair of said pin openings in the wall of said elongated rod;

(iv) boring a first opening in the adjacent cortical of the bone for receiving a fixation pin;

(v) introducing a bone boring device from said bone exterior, first through said first opening made in said bone cortical and one opening in said pair of pin openings in said elongated wall and then into the second pin opening of said pair of pin openings in said intramedullary device;

(vi) boring a second opening in the adjacent cortical of said bone for receiving a fixation pin, and (vii) introducing a pin through said openings for fixation of the intramedullary device to said bone.

12. The method of claim 11 wherein said baffle means is adapted for remaining in said central cavity of said intramedullary rod with fixation of said device to said bone tissue.

13. The method of claim 12 wherein said intramedullary device is introduced into the medullary cavity of said injured bone beginning at the proximal end of said bone.

14. The method of claim 12 wherein said intramedullary device is introduced into the medullary cavity of said injured bone beginning at the distal end of said bone for retrograde insertion.

15. The method of claim 11 wherein said bone boring device is selected from the group consisting of a drill bit, laser beam and ultrasonic mechanical energy.

16. The method of claim 11 wherein the baffle means of said intramedullary device comprises a narrowing and sloping passage.

17. The method of claim 11 wherein said baffle means of said intramedullary device is characterized by a funneling configuration for guiding said means for boring through bone tissue through rounded conduit means running in a direction generally normal to the longitudinal axis of said outer wall.

18. The method of claim 11 wherein the intramedullary device comprises a general nail-like configuration and the plane of a pair of said pin openings in said device is inclined obliquely to the longitudinal axis of said elongated rod.

19. The method of claim 18 wherein the intramedullary device comprises at least one pair of leading end pin openings and at least one pair of trailing end pin openings; the leading end of the device being fixed first by the introduction of an orthopedic pin through injured bone and through the leading end pin openings followed by fixation of the trailing end of the device by the introduction of an orthopedic pin through injured bone and the trailing end pin openings.

20. The method of claim 11 wherein the intramedullary device comprises a general nail-like configuration and the plane of a pair of said pin openings is positioned substantially normal to the longitudinal axis of said elongated rod.

* * * * *